(12) United States Patent
Kowalewski

(10) Patent No.: US 12,090,679 B2
(45) Date of Patent: Sep. 17, 2024

(54) SYRINGE CUTTER

(71) Applicant: PRP TECHNOLOGIES INC., Calgary (CA)

(72) Inventor: Marcin Kowalewski, Calgary (CA)

(73) Assignee: PRP TECHNOLOGIES INC, Calgary (CA)

(*) Notice: Subject to any disclaimer, the term of this patent is extended or adjusted under 35 U.S.C. 154(b) by 0 days.

(21) Appl. No.: 18/038,560

(22) PCT Filed: Jul. 26, 2021

(86) PCT No.: PCT/US2021/043175
§ 371 (c)(1),
(2) Date: May 24, 2023

(87) PCT Pub. No.: WO2023/009102
PCT Pub. Date: Feb. 2, 2023

(65) Prior Publication Data
US 2023/0398708 A1 Dec. 14, 2023

(51) Int. Cl.
*B26D 1/30* (2006.01)
*A61M 5/00* (2006.01)
(Continued)

(52) U.S. Cl.
CPC ............... *B26D 1/30* (2013.01); *A61M 5/008* (2013.01); *B26D 3/16* (2013.01); *B26D 7/01* (2013.01);
(Continued)

(58) Field of Classification Search
CPC ... B26D 1/30; B26D 3/16; B26D 7/01; B26D 2007/013; A61M 5/008; A61M 2207/10
See application file for complete search history.

(56) References Cited

U.S. PATENT DOCUMENTS 3,404,593 A * 10/1968 Arcarese ............ A61M 5/3278
83/167
3,469,750 A * 9/1969 Vanderbeck ........ A61M 5/3278
83/167

(Continued)

FOREIGN PATENT DOCUMENTS

| CN | 2915299 Y * | 6/2007 |
| KR | 102099964 B1 * | 2/2020 |
| WO | 2020/141759 | 7/2020 |

OTHER PUBLICATIONS

REZA27. "Syringe cutting tool" ... Web. Feb. 12, 2019; [Retrieved on Oct. 18, 2021]. 1—Retrieved from the internet: <url:https://3dprint.nih.gov/discover/3dpx-010519>; title; images 1-3.

*Primary Examiner* — Jonathan G Riley
(74) *Attorney, Agent, or Firm* — Jonathan D Feuchtwang

(57) ABSTRACT

Device for cutting a syringe having a barrel with a flange at a proximal end thereof, the barrel containing a liquid, a plunger provided in the barrel and sealing the liquid specimen therein, said cutting device comprising: a jig for supporting a syringe, the jig including a proximal wall and a distal wall, a first through-hole defined in the proximal wall and a second through-hole defined in the distal wall; wherein the first and second through-holes are coaxially aligned and are sized to closely approximate the barrel; the first through-hole including a counter bore such that a distal end of the first through-hole closely approximates the barrel and a proximal end of the first through-hole closely approximates the syringe flange; a blade pivotably supported between the proximal and distal walls; wherein the blade cuts the proximal end of the syringe with the flanges without contaminating the liquid within the barrel.

5 Claims, 29 Drawing Sheets

(51) Int. Cl.
   *B26D 3/16*      (2006.01)
   *B26D 7/01*      (2006.01)

(52) U.S. Cl.
   CPC ... *A61M 2207/10* (2013.01); *B26D 2007/013* (2013.01)

(56) References Cited

U.S. PATENT DOCUMENTS

| | | | | |
|---|---|---|---|---|
| 3,785,233 A * | 1/1974 | Robinson | ............ | A61M 5/3278 83/167 |
| 3,914,865 A * | 10/1975 | Oakes | ................ | A61M 5/3278 83/167 |
| 4,255,996 A * | 3/1981 | Choksi | ................ | A61M 5/3278 83/167 |
| 4,275,628 A * | 6/1981 | Greenhouse | ............. | B26D 5/10 83/167 |
| 4,404,881 A * | 9/1983 | Hanifl | .................... | B23D 15/12 83/167 |
| 4,565,311 A * | 1/1986 | Pugliese | ................ | B26D 1/09 83/167 |
| 4,584,917 A * | 4/1986 | Blom | ....................... | B26D 7/12 451/21 |
| 4,614,035 A * | 9/1986 | Andrews | ............ | A61M 5/3278 83/167 |
| 4,786,280 A * | 11/1988 | Maeda | ................ | A61M 5/3278 604/110 |
| 4,969,379 A * | 11/1990 | Taylor | .................... | B23D 21/00 83/167 |
| 5,138,125 A * | 8/1992 | Salesses | ................. | B23K 11/22 219/68 |
| 5,340,039 A * | 8/1994 | Lefevre | ............... | B02C 19/0075 241/94 |
| 5,467,930 A * | 11/1995 | Lefevre | .................. | B02C 18/02 241/94 |
| 5,468,928 A * | 11/1995 | Yelvington | ......... | A61M 5/3278 219/68 |
| 5,548,095 A * | 8/1996 | Cornell | ..................... | A61L 2/02 219/68 |
| 5,710,404 A * | 1/1998 | Descent | .................. | A61L 11/00 219/68 |
| 5,761,975 A * | 6/1998 | Waluda | ............... | A61M 5/3278 82/59 |
| 6,792,662 B2 * | 9/2004 | Samuel | ............... | A61M 5/3205 29/244 |
| 7,389,873 B2 * | 6/2008 | Johnson aka Mindes | .................... | A61M 5/3205 83/944 |
| 7,690,284 B2 * | 4/2010 | Cha | ..................... | A61M 5/3278 83/167 |
| 8,875,882 B1 * | 11/2014 | Salloum | ............. | A61M 5/3205 206/366 |
| 2007/0179443 A1 * | 8/2007 | Johnson aka Mindes | .................... | A61M 5/3205 604/110 |
| 2012/0246942 A1 | 10/2012 | Nie | | |
| 2013/0055575 A1 * | 3/2013 | Delmas | .................. | B26B 15/00 318/647 |
| 2014/0166624 A1 * | 6/2014 | Butler | .................. | A61M 5/3205 83/167 |
| 2020/0222640 A1 * | 7/2020 | Limaye | ................. | H05B 1/025 |

* cited by examiner

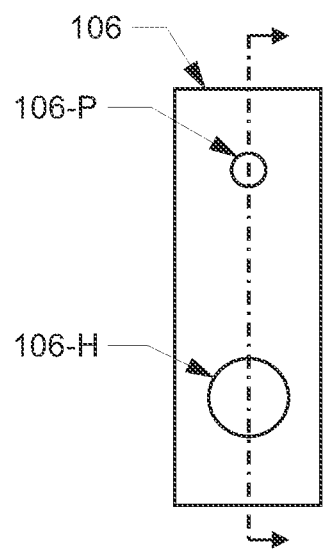
FIG. 2A
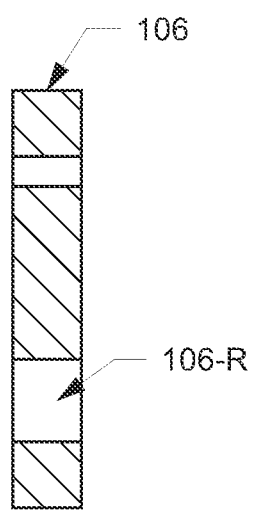 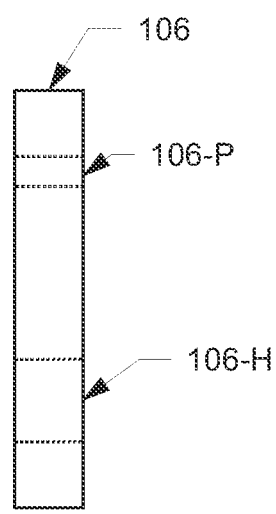
FIG. 2B
FIG. 2C

SYRINGE CUTTER

FIELD

The invention relates to a device and a method for converting a syringe filled with a specimen, into a tube holding the specimen, for insertion into a centrifuge. The invention clips or slices off the proximal end of the syringe with the flanges as well as a proximal portion of the syringe plunger thereby enabling the syringe with the specimen to be properly inserted into common laboratory centrifuges that can accommodate only small-diameter containers. This minimizes loss and possible contamination associated with transferring the specimen into a test tube.

The invention and the method have applications in chemical, biological, pharmaceutical, and medical fields where centrifugation takes place.

The process of preparing platelet rich plasma (PRP) and separation of platelet poor plasma (PPP) from whole blood are just some of many applications that benefit from the invention and the methods described herein.

BACKGROUND

Centrifuges are used in various procedures to separate liquid mixtures into distinct density layers or fractions. Most common laboratory centrifuges have small-diameter cavities and are unable to accommodate the popular syringes with flanges and plungers extending proximally from the barrel of the syringe.

Syringes often are a tool of choice for acquiring specimens for processing and are used as a transfer vehicle to dispense the specimen to other containers. Syringes are excellent for extraction and dispensing of fluids from various containers, such as specimen tubes and vials.

When operating a syringe, the flanges of the syringe provide an anchor for the operator's fingers when: 1) retracting the plunger out of the barrel (away from the flanges) of the syringe to acquire specimen, and 2) pushing the plunger into the barrel of the syringe to dispense specimen.

The flanges of a syringe extend orthogonally from the longitudinal axis of the barrel of the syringe, and the retracted plunger extends beyond the length of the barrel of the syringe. The extending plunger and the protruding flanges prevent such syringe from being properly inserted into the centrifuge specimen holder.

It is possible to cut off the flanges and the plunger with scissors. However, clipping the flanges with commonly available tools such as scissors or heavy-duty cutters, is challenging as it requires multiple cuts, produces debris, and risks cracking the barrel particularly if the syringe is cold and hence is more brittle, as is sometimes the case in hypothermic procedures. Conventional tools do not produce a perfectly flush-with-the-surface finish and the roughness and imperfections of the edges look unprofessional and often impede easy insertion into narrow centrifuge specimen holders. Importantly, none of the conventional tools are able to cut the flanges from a syringe containing a specimen without putting the specimen at risk of accidental spilling, contamination, or vibrational impact or shock with a potential to cause specimen degradation. What is needed is an improved cutter which is able to cut off the proximal portion of a conventional syringe, i.e., the end of the syringe with the flanges, containing a specimen without losing or contaminating the specimen. Moreover, what is needed is an improved cutter which is able to produce a clean cut of a chilled polypropylene syringe containing a specimen, without cracking the syringe barrel.

SUMMARY OF THE INVENTION

Example 1. A device for cutting a syringe having a barrel with a flange at a proximal end thereof, the barrel containing a liquid specimen, a plunger provided in the barrel and sealing the liquid specimen therein, said cutting device comprising:
  a jig for supporting a syringe, the jig including a proximal wall and a distal wall, a first through-hole defined in the proximal wall and a second through-hole defined in the distal wall;
  wherein the first and second through-holes are coaxially aligned and are sized to closely approximate the barrel;
  the first through-hole including a counter bore such that a distal end of the first through-hole closely approximates the barrel and a proximal end of the first through-hole closely approximates the syringe flange; and
  a blade pivotably supported between the proximal and distal walls;
  wherein the blade cuts the proximal end of the syringe with the flanges and the plunger without contaminating the liquid specimen within the barrel.

Example 2. The cutting device of Example 1, further comprising a flange sensor proximal to the counterbore, said flange detector detecting the presence of a flange in the counterbore.

Example 3. The cutting device of Example 1, further comprising at least one position sensor proximal to the blade, said position sensor detecting a position of the blade assembly.

Example 4. The device of Example 2, further comprising at least one indicator light for indicating an operating state of the cutting device.

Example 5. The device of Example 2, further comprising a processor operably connected to the flange sensor and inhibiting operation of the cutting device unless the flange detector detects a flange within the counterbore.

Example 6. The device of Example 1, further comprising:
  a third through-hole defined in the proximal wall, a fourth through-hole defined in the distal wall, and a fifth through hole defined in the blade;
  a pin inserted into the third, fourth, and fifth through-holes, said pin movably coupling the blade to the proximal and distal walls.

Example 7. A device for cutting a syringe having a barrel with a flange at a proximal end thereof, the barrel containing a liquid specimen, a plunger provided in the barrel and sealing the liquid therein, said cutting device comprising:
  a jig for supporting a syringe, the jig including a proximal wall including a first portion P1 and a second portion P2, a distal wall including a first portion D1 and a second portion D2, and a blade sandwiched between the proximal and distal walls;
  a first through-hole defined in P1, a second through hole defined in P2, a third through-hole defined in D1, and a fourth through-hole defined in D2;
  a pin inserted into the first, second, third and fourth through-holes thereby allowing P2 and D2 to pivot with respect to P1 and D1;
  the blade pivotably supported between the proximal and distal walls;
  the proximal wall having a sixth through-hole, a proximal end of the sixth through-hole including a counterbore, the sixth through-hole cooperatively defined by recess P1-SR defined in P1 and recess P2-SR in P2 when the jig is in a closed position with P1 abutting P2, wherein the counterbore is configured to closely approximate the flange of the syringe;

the distal wall having a seventh through-hole, the seventh through-hole cooperatively defined by semicircular recess D1-SR defined in D1 and semicircular recess D2-SR in D2 when the jig is in a closed position with D1 abutting D2, wherein a diameter of the seventh through-hole is configured to closely approximate the barrel of the syringe;

wherein the blade cuts the proximal end of the syringe barrel and syringe plunger without contaminating the liquid specimen within the barrel.

Example 8 The cutting device of Example 7, further comprising a fifth through-hole defined in the blade, the pin extending through the fifth through-hole.

Example 9. The cutting device of Example 7, further comprising a flange sensor proximal to the counterbore, said flange detector detecting the presence of the flange in the counterbore.

Example 10. The cutting device of Example 7, further comprising at least one position sensor proximal to the blade, said position sensor detecting a position of the blade.

Example 11. The device of Example 9, further comprising at least one indicator light for indicating an operating state of the cutting device.

Example 12. The device of Example 9, further comprising a processor operably connected to the flange sensor and inhibiting operation of the cutter unless the flange sensor detects a flange within the counterbore.

BRIEF DESCRIPTION OF THE DRAWINGS

FIGS. 2A-2C are a side view, a sectional view, and a top view of the distal wall 106;

DETAILED DESCRIPTION

Disclosed is a device and associated method for cutting a conventional polypropylene syringe 102 used to inject/withdraw fluids to/from a patient. More particularly, disclosed is a device and associated method for cutting the flanges from a conventional polypropylene syringe 102 containing a specimen. According to another aspect, the device of the present invention is capable of cutting a conventional polypropylene syringe 102 containing a specimen where the syringe has been chilled to preserve the specimen, without cracking the syringe 102 or contaminating the specimen. The disclosed device 100 slices off the proximal end of the barrel with flanges still attached and the plunger without contaminating a specimen within the barrel. A device according to the present invention clips the proximal end of the barrel of the syringe and a proximal end of the syringe plunger. The device 100 produces a clean cut without jagged edges and does not crack the syringe barrel or expel the contents of the syringe. Polypropylene syringes are very prone to cracking, especially when being cut under hypothermic conditions, which are sometimes required to preserve the specimen in the syringe. Proper alignment of the cutting blade, mechanical restriction of the barrel from even miniscule deformations under the pressure of the blade, as well as support of the flexing barrel end, are paramount for a clean cut and for protecting the specimen inside.

The ability to acquire specimen within a syringe and insert the syringe into the centrifuge without the need to transfer the specimen to a different container, reduces the risk of specimen loss, reduces the risk of specimen contamination, reduces the risk of specimen degradation, and reduces the number of components needed in the process, which lowers the cost and minimizes the waste. It also allows the specimen to be transferred out after centrifugation, by pushing the plunger in with a finger, a pen, or another syringe.

An important object of the invention is to provide a device capable of cleanly cutting the flanges from a chilled syringe containing a specimen without cracking the syringe or contaminating the specimen contained therein.

Figure 1A:
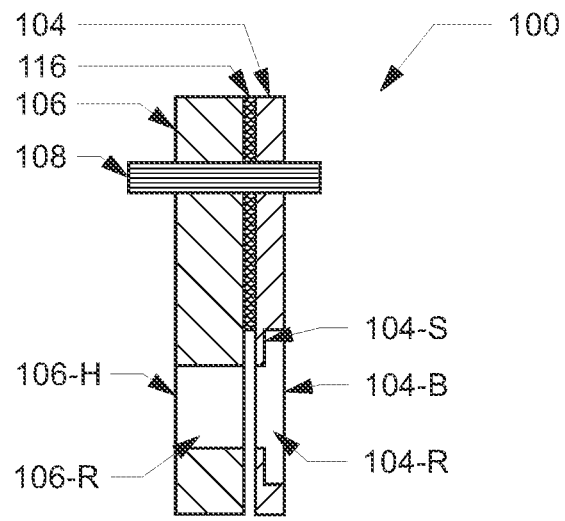
FIGS. 1A-1B is a top view of a horizontal cross-section and a side view of an example cutter without a syringe.
Figure 1B:
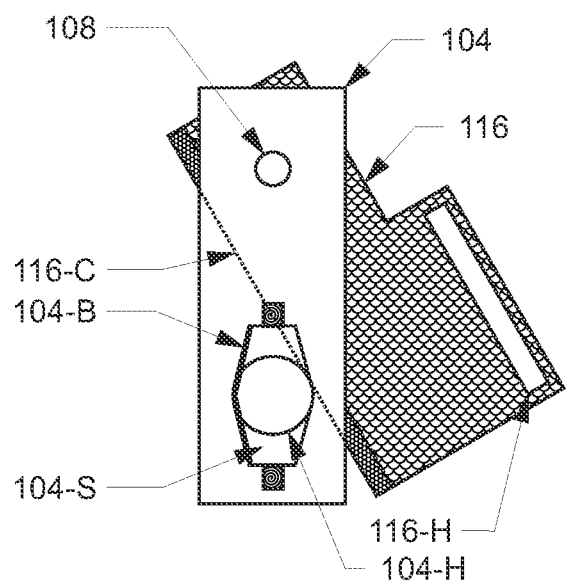
Figure 1C:
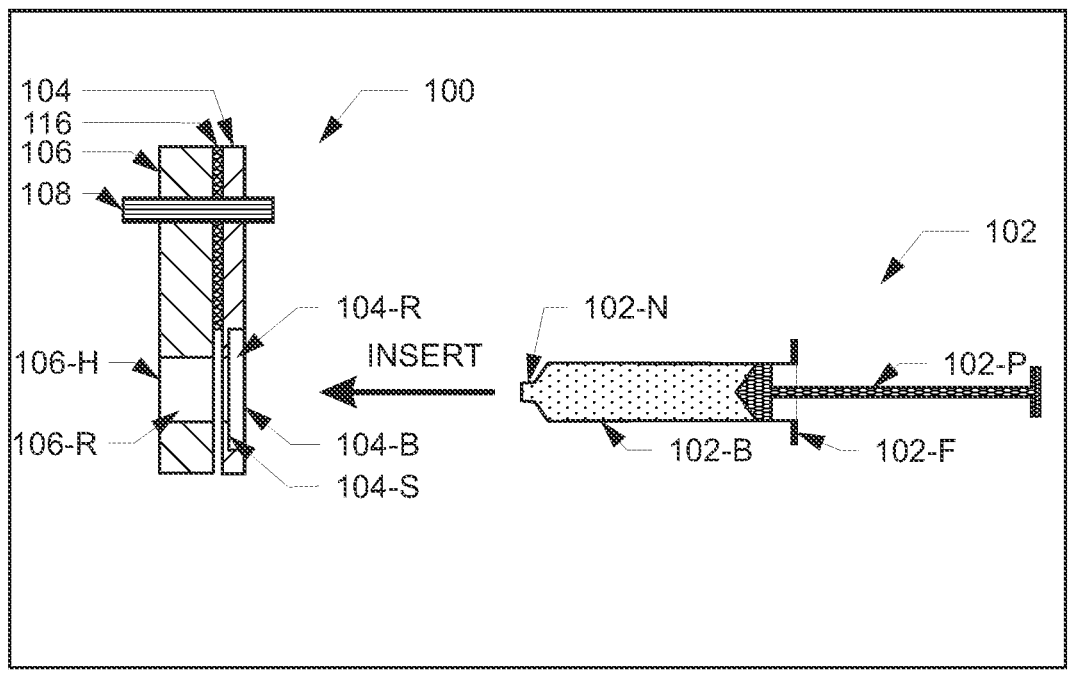
FIG. 1C shows a syringe being inserted into the cutter of FIG. 1A.

FIGS. 1A-1B is a top view of a horizontal cross-section and a side view of an example syringe cutter 100. FIG. 1C shows a syringe 102 being inserted into the cutter of FIG. 1A. In its most elementary form, the device 100 is a jig which accommodates and supports a conventional polypropylene syringe 102. The device 100 includes a proximal wall 104, and a distal wall 106 which are parallel and sandwich blade 116 which is rotatably mounted therebetween. FIG. 1C shows the process for inserting a polypropylene syringe 102 into a device 100 of FIG. 1A.

FIGS. 2A-2C are side view, sectional view, and a top view of the distal wall 106. Distal wall 106 is provided with through-holes 106-H and 106-P. Through-hole 106-P is sized to receive a pin 108 (FIG. 1A). Through-hole 106-H is sized to snugly receive a barrel portion of conventional syringe 102 (not shown). The interior circumference 106-R of through-hole 106-H is selected to closely approximate the exterior circumference of the barrel of the syringe 102 (not shown).

Figure 3A:
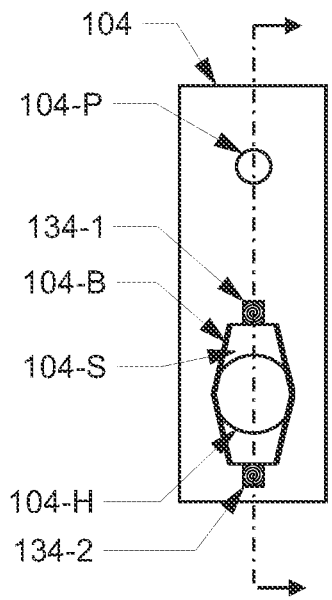
FIGS. 3A-3C are a side view, a sectional view, and a top view of A1 the proximal wall 104.
Figure 3B:
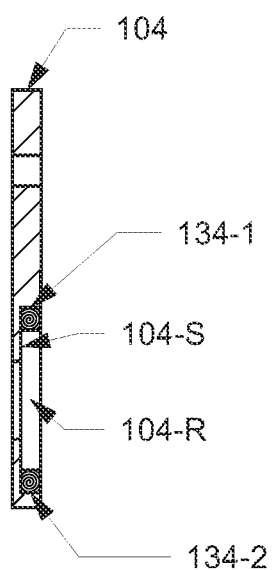
Figure 3C:
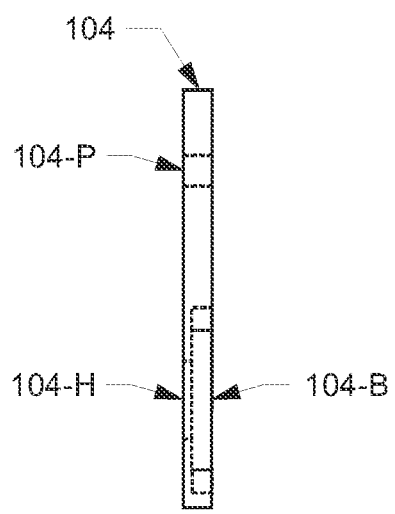

FIGS. 3A-3C are a side view, a sectional view, and a top view of the proximal wall 104. Proximal wall is provided with through-holes 104-H and 104-P. Through-hole 104-P is sized to receive a pin 108 (FIG. 1A). Through-hole 104-H is sized to snugly receive a barrel of a conventional syringe 102 (FIG. 1C). Through-hole 104-H includes a proximal counterbore 104-B which is sized to snugly receive the proximal end of the syringe 102 including flanges 102-F. The counterbore 104-B includes a surface 104-S which limits the depth of insertion of the syringe 102, and further includes a surface 104-R which follows the interior perimeter of the counterbore portion 104-B of through-hole 104-H. According to one example, the perimeter 104-R is configured to support the flanges 102-F when the blade 116 is cutting the barrel. In other words, the surface 104-R is selected to closely approximate at least a portion of the flanges 102-F of the syringe 102 such that the proximal end of the syringe is supported.

The proximal wall 104 may be equipped with one or more sensors 134 such as a limit switch or the like to detect the presence of flanges 102-F. In FIG. 3A, two sensors 134-1 and 134-2 are provided near the counterbore portion 104-B of through-hole 104-H. The counterbore 104-B has a first portion 104-S (FIG. 3A) which is generally parallel to the plane of the flanges 102-F, and a second portion 104-R which is generally orthogonal to surface 104-S. Portions 104-S and 104-R are configured to firmly engage with the flanges 102-F when the syringe is fully inserted into through-hole 104-H. This ensures accurate and repeatable insertion of syringes 102 into device 100 and ensures that the proximal portion of the syringe 102 is firmly supported during the cutting process. The sensor 134 may be operably connected to a controller (not illustrated) which selectively permits actuation of the blade 116 if the sensor 134 detects the flange 102-F and otherwise inhibits operation of the blade 116. In some examples, indicator lights (not illustrated) operably connected to the controller (not illustrated) may be used to visually indicate the operational status of the device. For example, a green light may indicate that the device has identified the presence of a flange 102-F and is ready to cut, whereas a red light may indicate that the device 100 is not ready to cut. In some examples, the device 100 may be equipped with one or more sensors 134 to make determination whether or not a syringe has been inserted as opposed to an object which is not a syringe, such as a pen or a finger.

In some examples, the device 100 may be equipped with sensors or the like which engage with the blade 116 to determine the position of the blade throughout the cutting process.

Figure 4A:
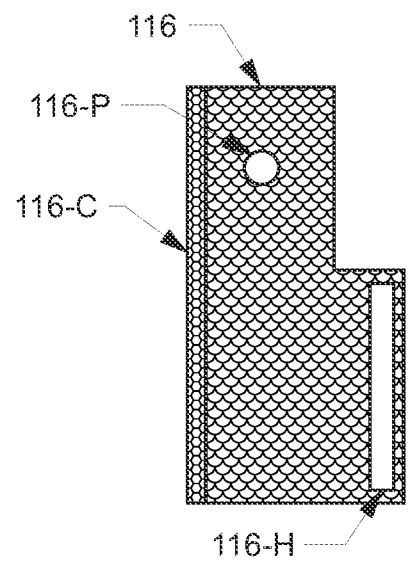
FIGS. 4A-4C show different shapes of blade 116.
Figure 4B:
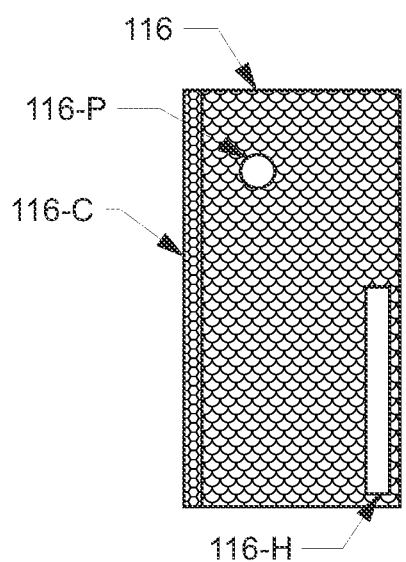
Figure 4C:
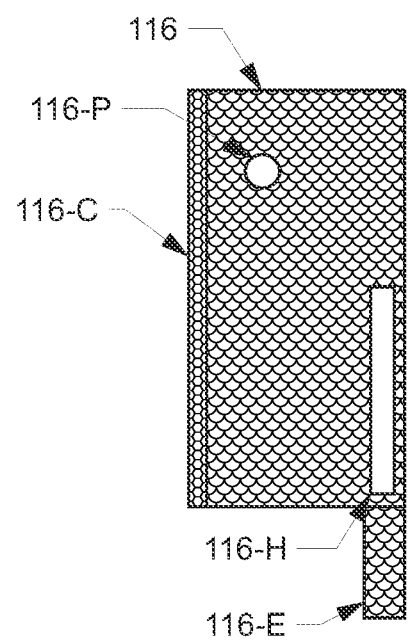

FIG. 4A-4C show different configurations of blade 116. The cutting surface 116-C of the blade may be single or double beveled as desired. Blade 116 includes a through-hole 116-P which is sized to receive pin 108 (FIG. 1A). Blade 116 may be provided with through-hole 116-H which is configured to operatively engage with a motor (not illustrated) used to drive the blade during cutting. The invention is not limited to any particular shape of through-hole 116-H. The overall shape of the blade in FIGS. 4A-4C is different to show that the invention is not limited to a particular shape. The blade 116 may be mounted directly on pin 108 or maybe mounted on a blade holder (not shown) having a through-hole sized to receive pin 108.

Turning back to FIG. 1A, the proximal wall 104 and distal wall 106 sandwich and support blade 116 during the cutting process to ensure a clean cut. More particularly, blade 116 may move relative to the proximal and distal walls 104, 106 which are fixed. Pin 108 is received in through-holes 104-P, 116-P, and 106-P. Pin 108 serves as a pivot point for the blade, and aligns the proximal wall, distal wall, and blade relative to one another.

As shown in FIG. 1C, the syringe 102 is inserted from right-to-left such that the needle hub 102-N of the syringe 102 is inserted sequentially through the 104-H and 106-H, with the flanges 102-F seated within counterbore 104-B and engaged with walls 104-R, 104-S.

Figure 5A:
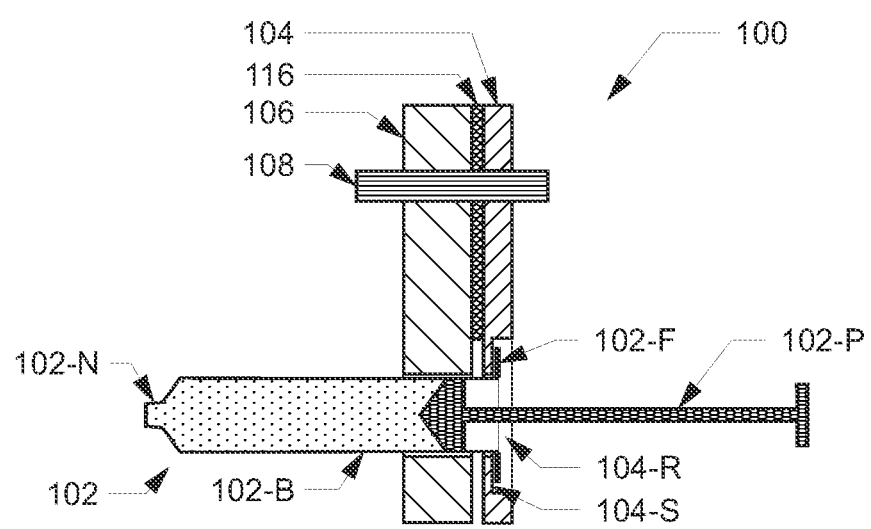
FIG. 5A is a top view of a horizontal cross-section of the cutter of FIG. 1A prior to initiating cutting of the syringe barrel.

FIG. 5A is a top view of a horizontal cross-section of the cutter of FIG. 1A showing the flanges 102-F seated within bore 104-B with blade 116 in a position prior to initial cutting.

Figure 5B:
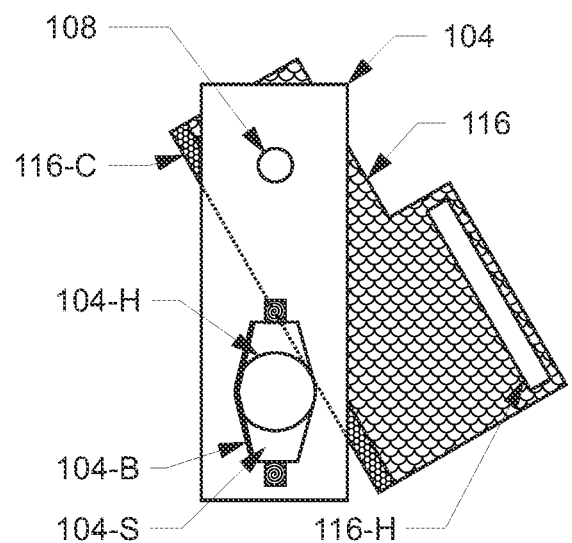
FIGS. 5B and 5C are side views of FIG. 5A with and without the syringe.
Figure 5C:
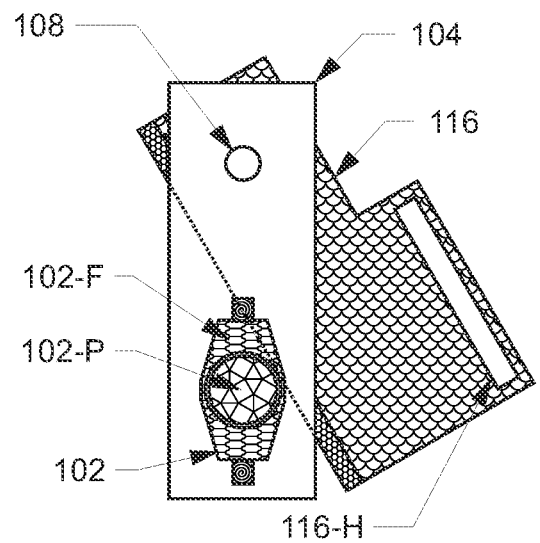

FIGS. 5B and 5C are side views of FIG. 5A without and with the syringe.

Figure 6A:
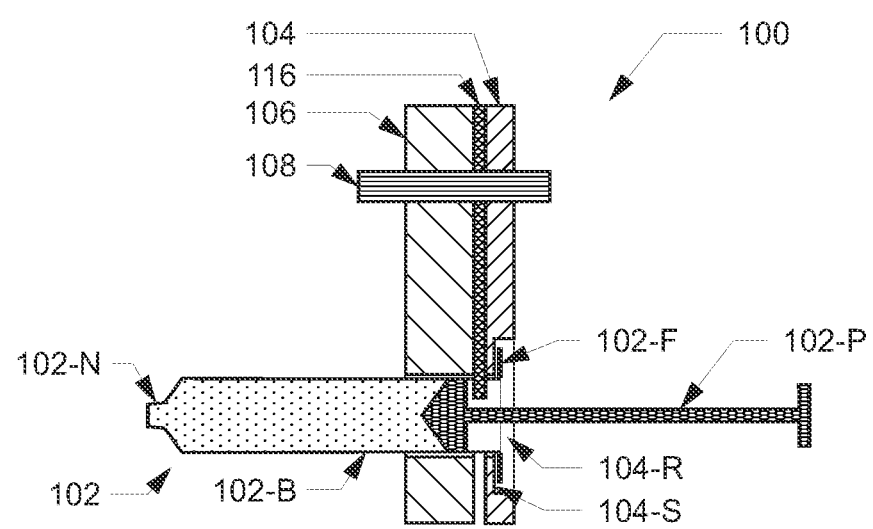
FIG. 6A is a top view of a horizontal cross-section of a syringe inside of the cutter of FIG. 1A making the initial cut of the syringe barrel.

FIG. 6A is a top view of a horizontal cross-section of a syringe inside of the cutter of FIG. 1A showing the flanges 102-F seated within counterbore 104-B with blade 116 in an initial cutting position. Cutting edge 116-C has made an initial cut into the barrel 102-B of the syringe 102.

Figure 6B:
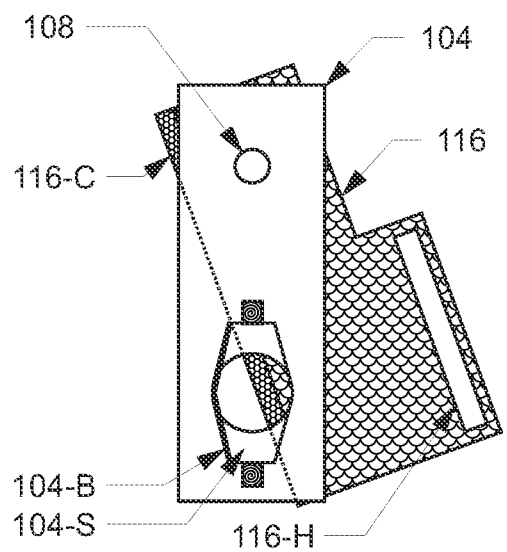
FIGS. 6B and 6C are side views of FIG. 6A with and without the syringe.
Figure 6C:
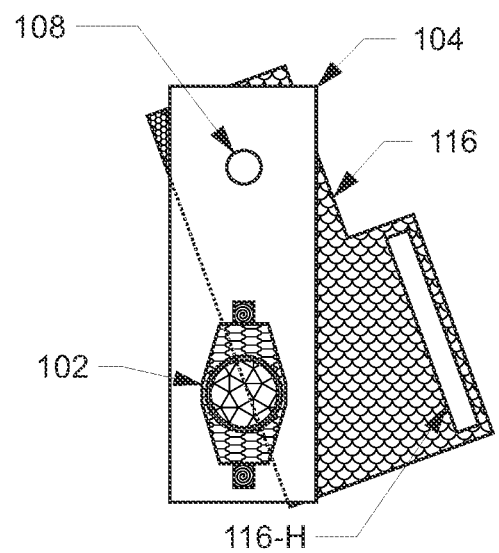

FIGS. 6B and 6C are side views of FIG. 6A without and with the syringe. In FIG. 6B the cutting edge 116-C of blade 116 is visible through the through-hole 104-H.

Figure 7A:
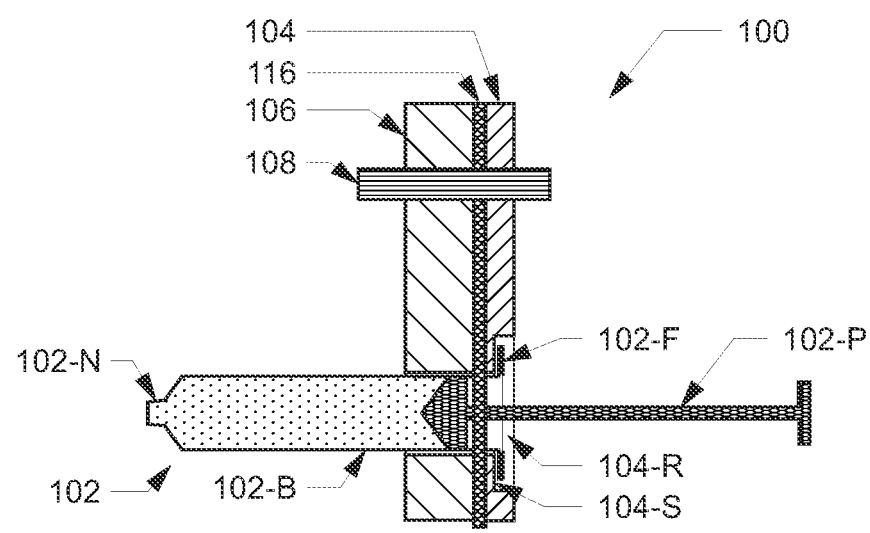
FIG. 7A is a top view of a horizontal cross-section of a syringe inside of the cutter of FIG. 1A making the final cut of the syringe barrel.

FIG. 7A is a top view of a horizontal cross-section of a syringe inside of the cutter of FIG. 1A showing the flanges 102-F seated within counterbore 104-B with blade 116 in a final cutting position. Cutting edge 116-C has cut through the barrel 102-B and plunger 102-P of the syringe 102.

Figure 7B:
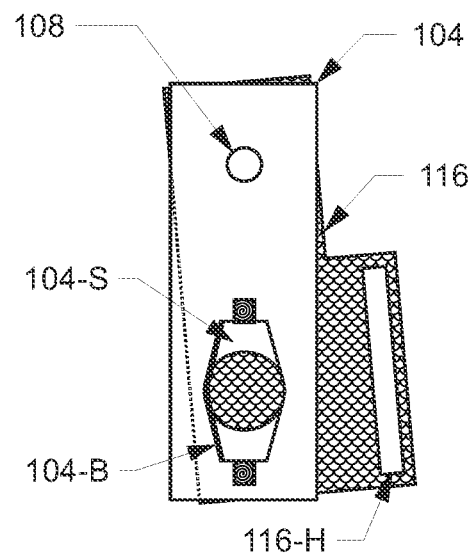
FIGS. 7B and 7C are side views of FIG. 7A with and without the syringe.
Figure 7C:
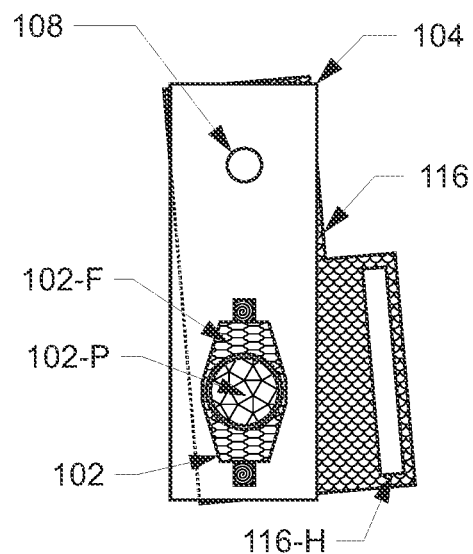

FIGS. 7B and 7C are side views of FIG. 7A without and with the syringe. In FIG. 7B the blade 116 is shown fully occluding the through-hole 104-H.

Hinged Two-Piece Configuration

Figure 8A:
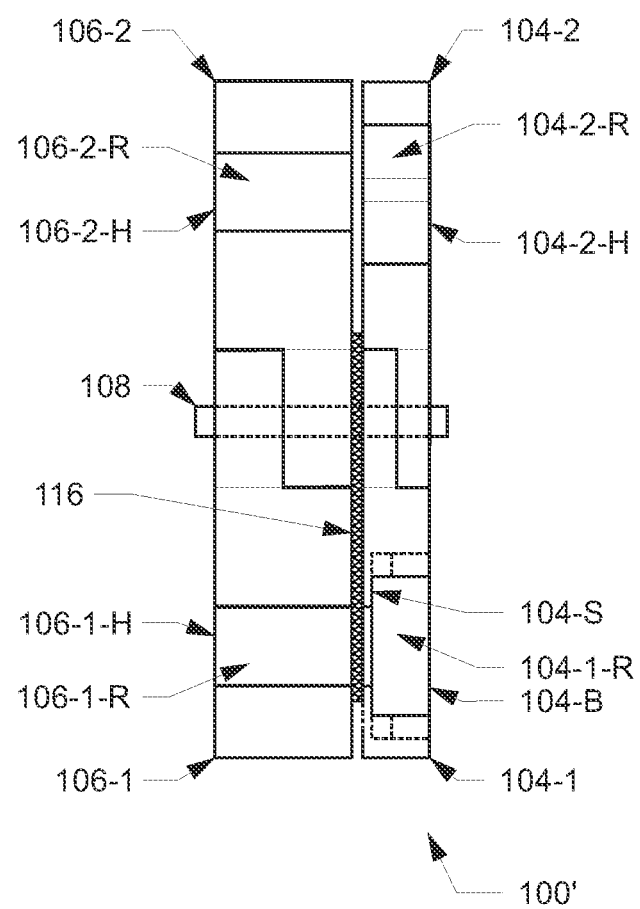
FIGS. 8A-8B is a top view and a side view of jig 100' in which the proximal and distal walls from FIG. 1 are each formed of two complimentary shaped pieces.
Figure 8B:
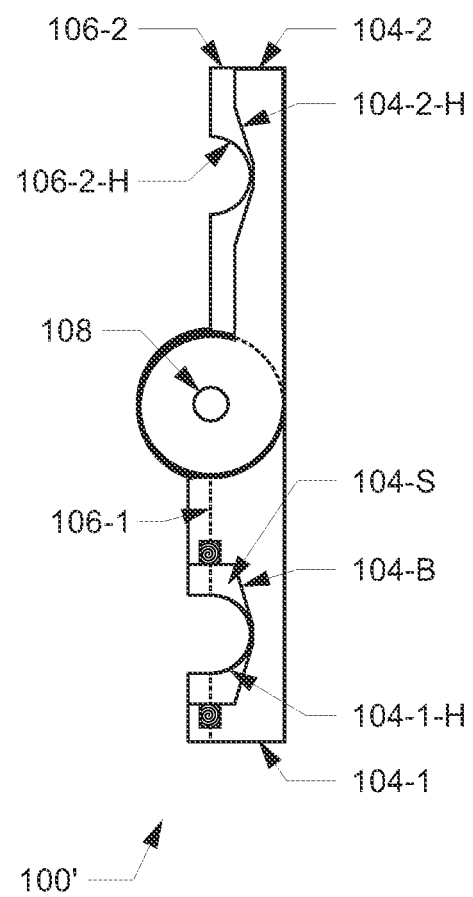

According to one example, a two-piece configuration of the syringe cutter 100' is disclosed. The two-piece configuration 100' resembles a stapler. In FIGS. 8A-8B, the cutter 100' is shown in the open position. In FIG. 8B the blade 116 is removed for clarity. In the two-piece configuration 100' the proximal and distal walls 104, 106 are each split into two complimentary shaped pieces 104-1, 104-2, 106-1 and 106-2. The two complimentary shaped pieces of the proximal wall 104-1 (P1), 104-2 (P2) are generally mirror images; however, there are some differences in the counterbore 104-B (104-1-R and 104-2-R). The two complimentary shaped pieces of distal wall 106-1 (D-1), 106-2 (D2) (FIGS. 8A-8B) are mirror images. Also cut in half are through-holes 104-P (104-1-P, 104-2-P), and 106-P (106-1-P, 106-2-P).

The through-hole 106-H is cooperatively defined by a semi-circular recesses 106-1-H, 106-2-H defined in distal wall 106-1 (D1) and 106-2 (D2). FIGS. 9C-9E.

Figure 8C:
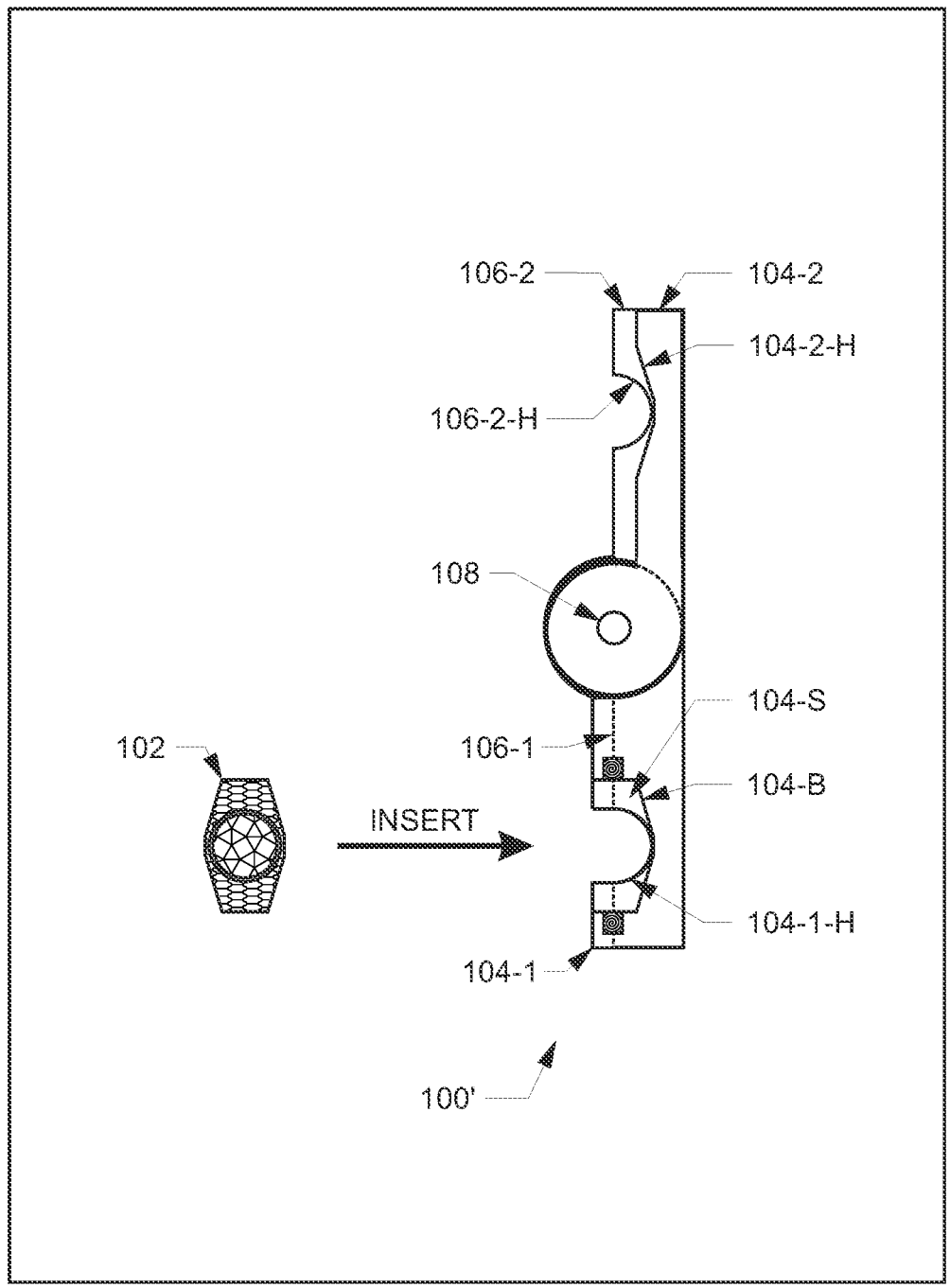
FIG. 8C is a side view of device 100' showing how syringe 102 is inserted.

FIG. 8C is a side view of device 100' showing how a syringe 102 is inserted.

Figure 8D:
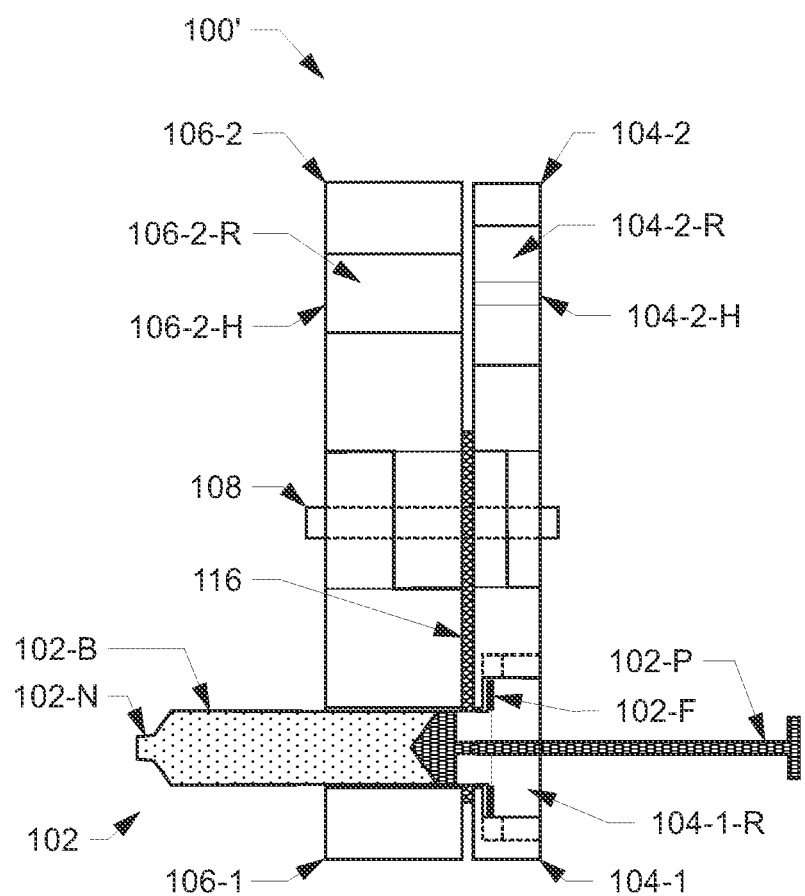
FIGS. 8D-8E is a top view and a side view of the device of FIGS. 8A-8B with a syringe 102 inserted therein prior to initiating cutting of the syringe barrel.
Figure 8E:
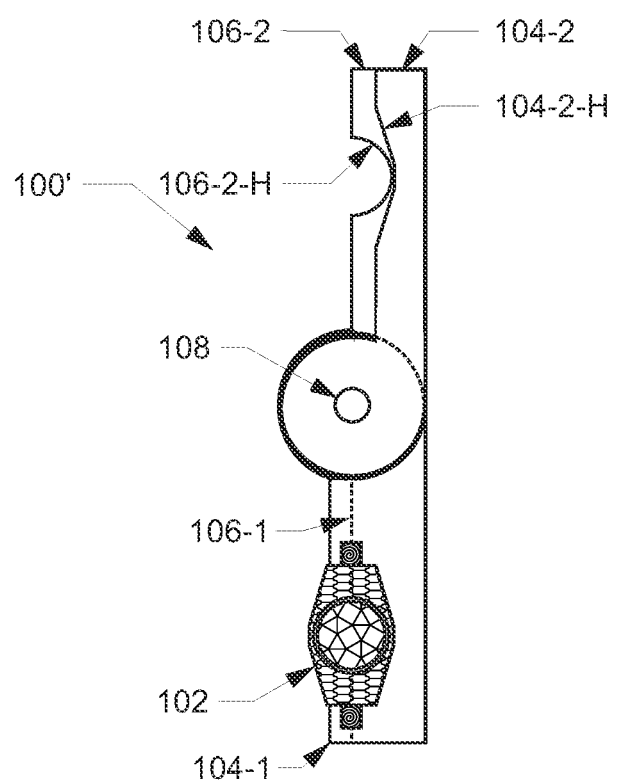

FIGS. 8D-8E is a top and side view of cutter 100' in an open position with syringe 102 inserted. In FIG. 8E the blade 116 is removed for clarity.

Figure 8F:
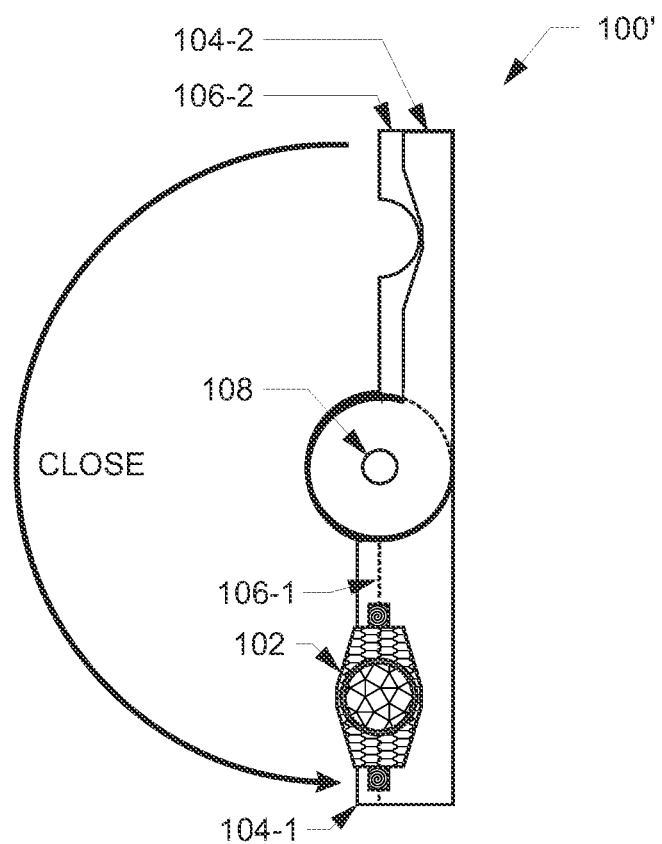
FIGS. 8F-8G show side views of the device of FIG. 8D in open and closed positions with syringe 102 inserted and with the blade 116 removed for clarity.
Figure 8G:
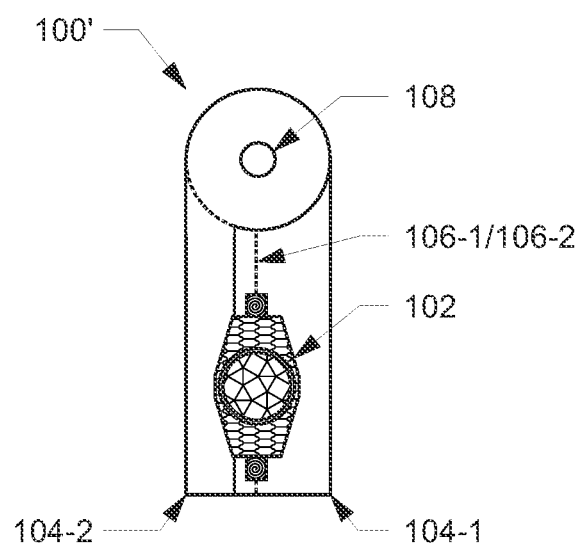

FIGS. 8F-8G are side views of cutter 100' in open and closed positions with syringe 102 inserted and with the blade 116 removed for clarity.

Figure 9A:
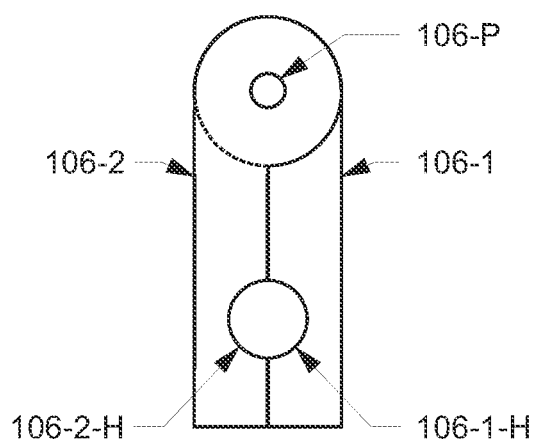
FIGS. 9A-9B are side and top views of distal wall portions 106-1 and 106-2 in a closed position.
Figure 9B:
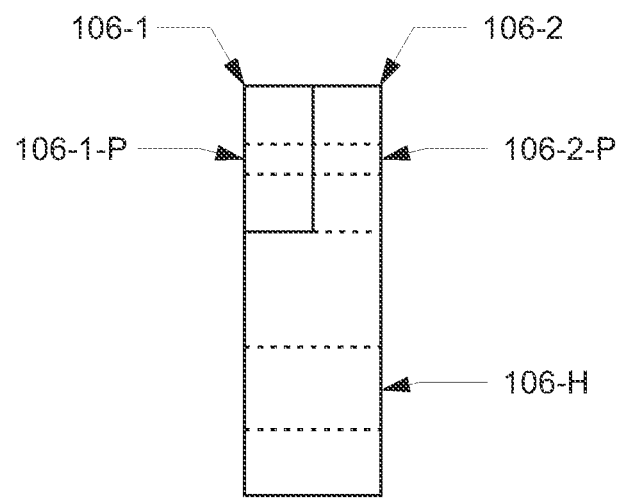
Figure 9C:
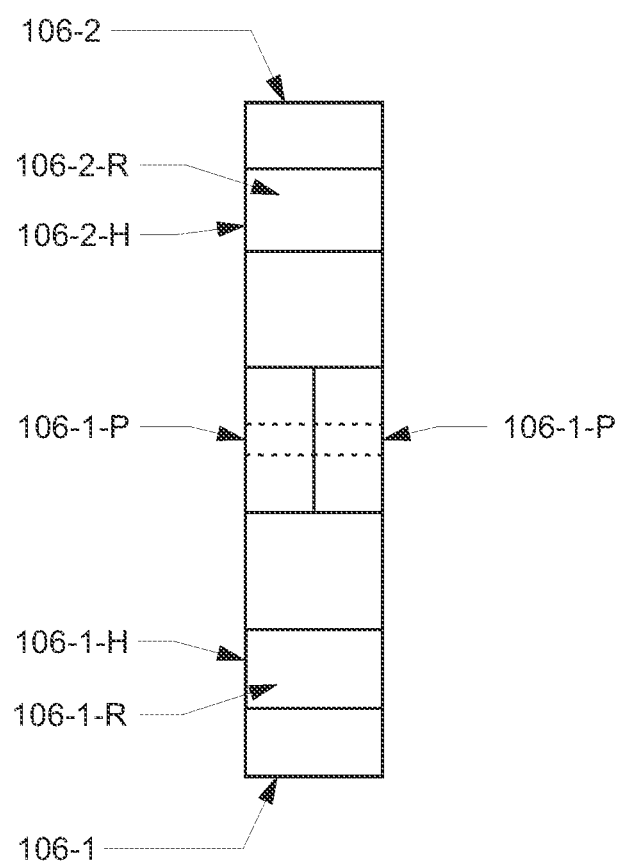
FIGS. 9C-9E is a top view, right side view and left side view of distal wall in an open position with blade removed for clarity.
Figures 9D, 9E:
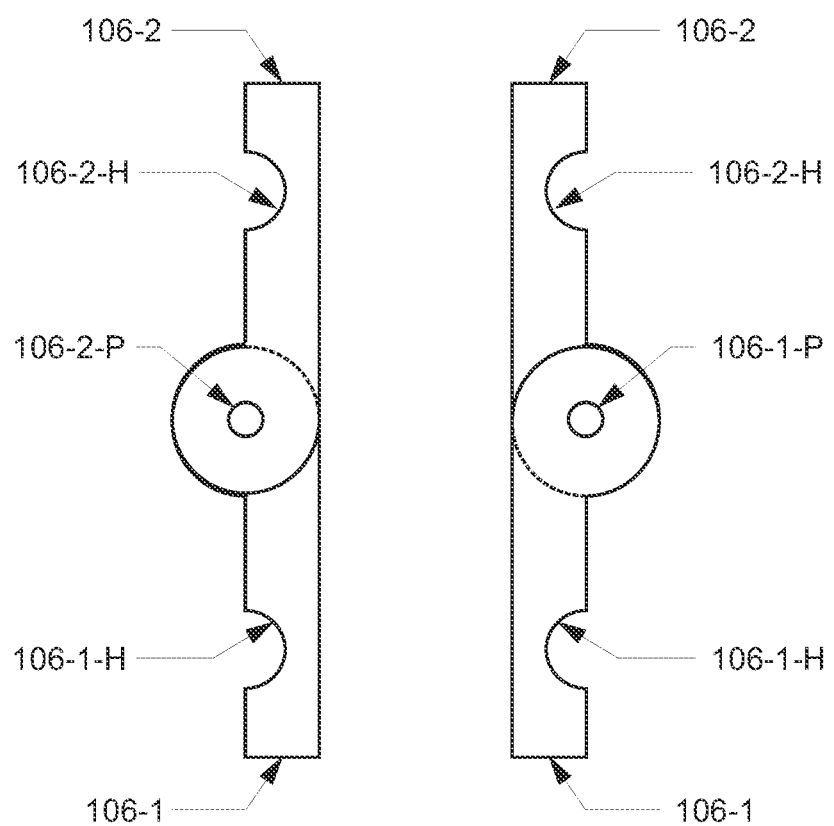

FIGS. 9A-9B are side and top views of distal wall portions 106-1 and 106-2 in a closed position.

FIGS. 9C-9E is a top, right side view and left side view of distal wall portion 106-1 and 106-2 in an open position with blade removed for clarity.

Figure 10A:
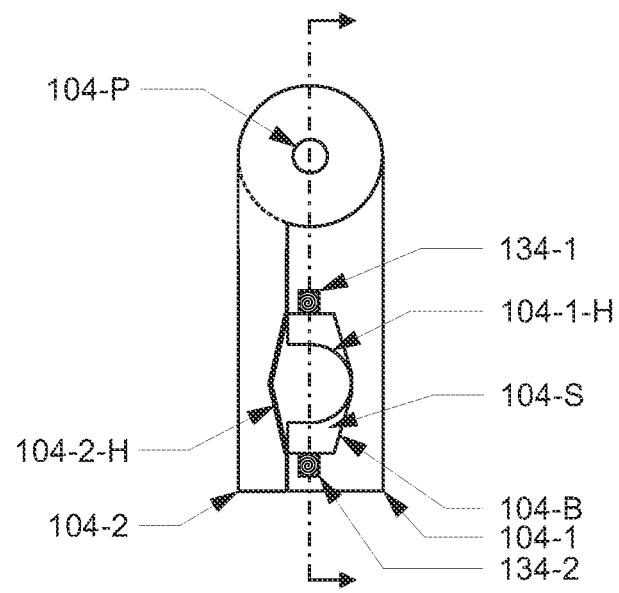
FIGS. 10A-10B are right side and sectional views of proximal wall in a closed position.
Figure 10B:
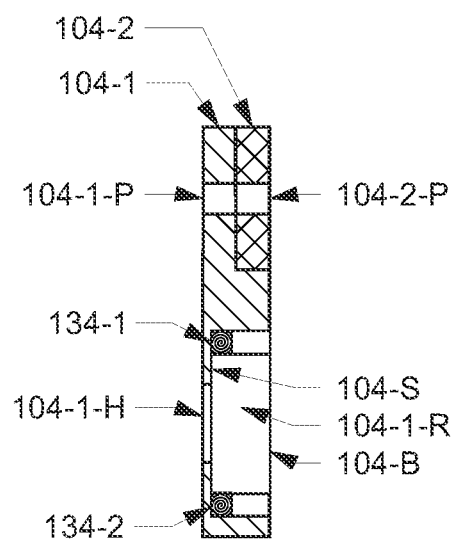

FIGS. 10A-10B are right side and sectional views of proximal wall portions 104-1 and 104-2 in a closed position. The dashed line in FIG. 10A designates the cross-section used to create FIG. 10B.

Figure 10C:
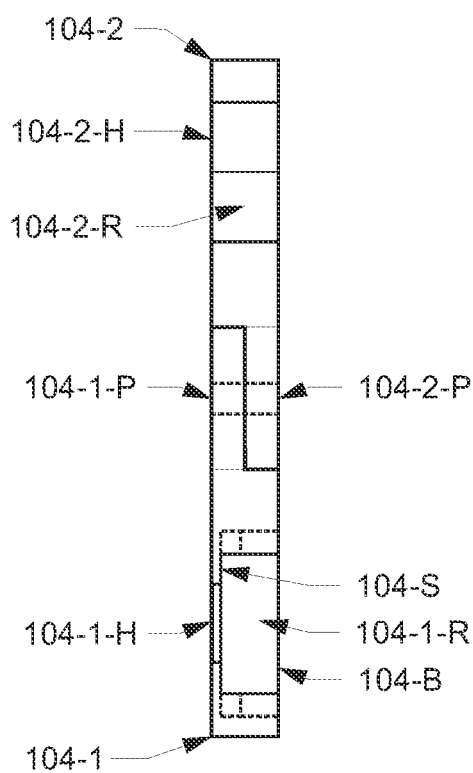
FIGS. 10C-10E is a top, right side view and left side view of proximal wall in an open position with blade removed for clarity.
Figure 10D:
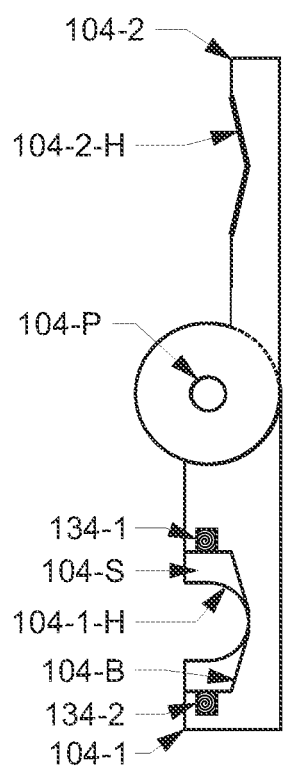
Figure 10E:
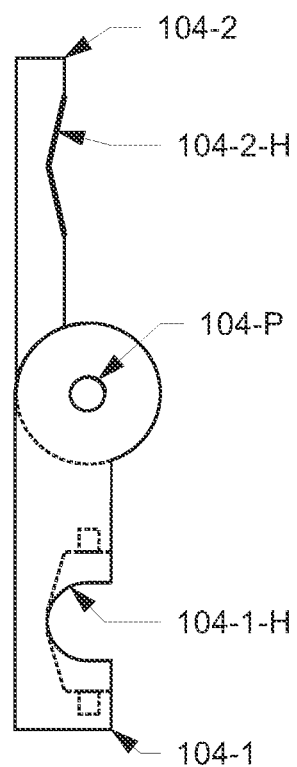

FIGS. 10C-10E is a top, right side view and left side view of proximal wall portions 104-1 and 104-2 in an open position with blade 116 removed for clarity.

Figure 11A:
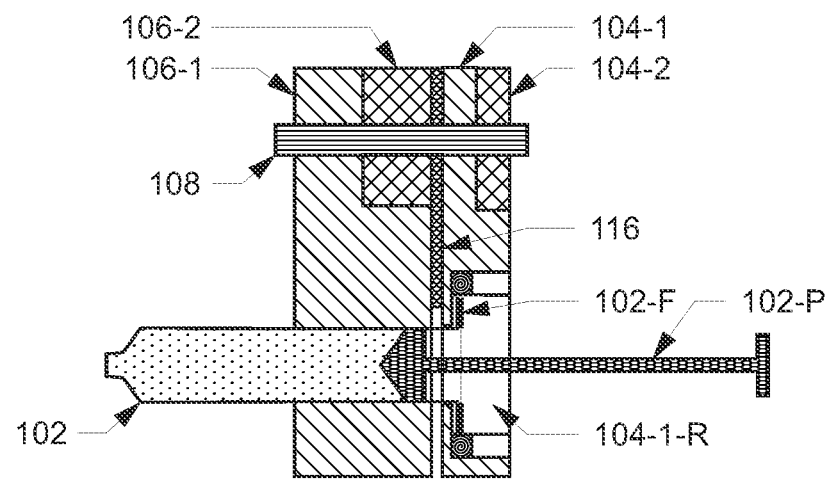
FIG. 11A shows a device according to FIG. 8D prior to initiating cutting of the syringe barrel.
Figure 11B:
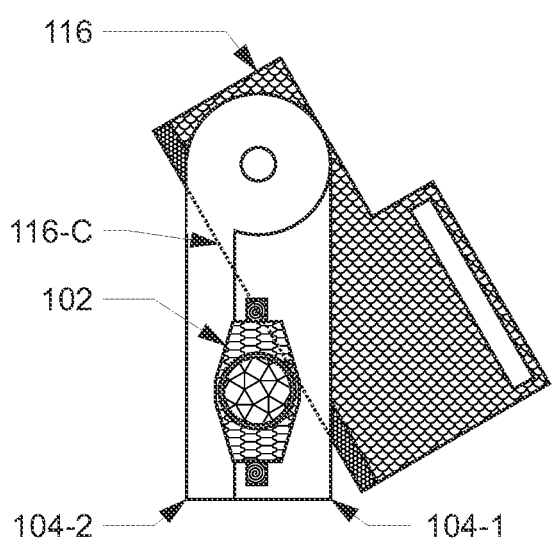
FIG. 11B is a side view of FIG. 11A.

FIG. 11A shows a device according to FIG. 8D prior to initiating cutting of the syringe barrel. FIG. 11B is a right-side view of FIG. 11A.

Figure 11C:
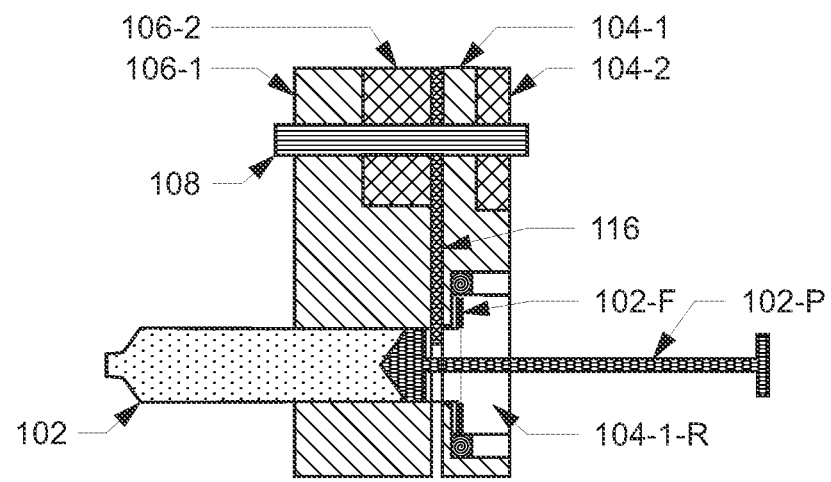
FIG. 11C shows a device according to FIG. 8D making the initial cut of the syringe barrel.
Figure 11D:
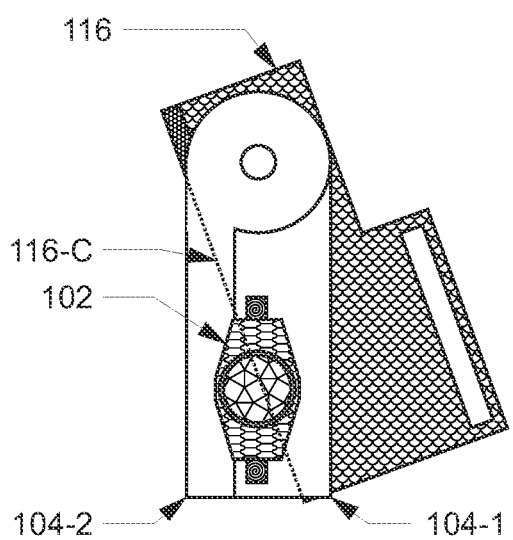
FIG. 11D is a side view of FIG. 11C.

FIGS. 11C-11D show the device of FIG. 11A with the blade 116 making the initial cut into the syringe 102. As best seen in FIG. 11C the cutting edge 116-C is extending into the syringe 102.

Figure 11E:
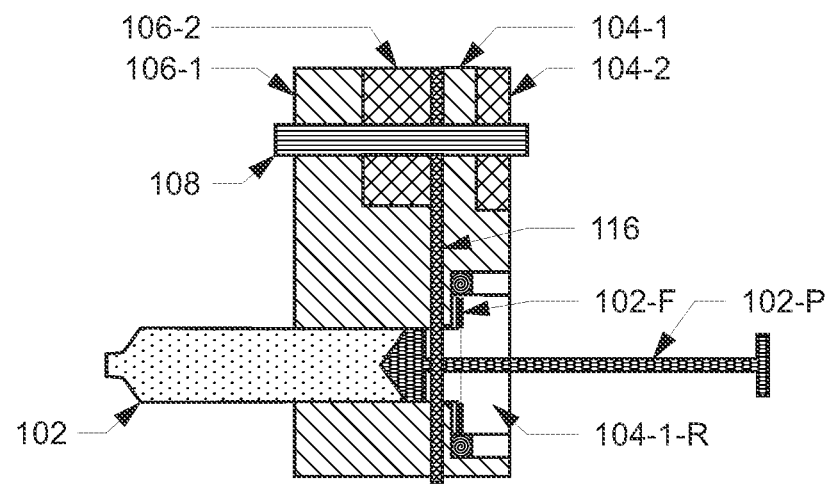
FIG. 11E shows a device according to FIG. 8D making the final cut of the syringe barrel.
Figure 11F:
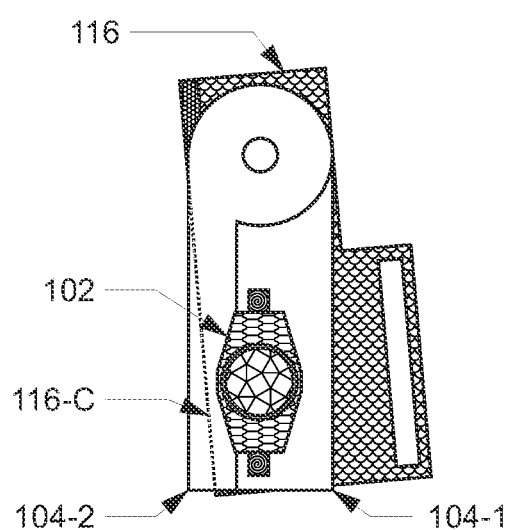
FIG. 11F is a side view of FIG. 11E.

FIGS. 11E-11F show the device of FIG. 11A with the blade 116 making the final cut into the syringe 102. As best seen in FIG. 11E the blade 116 extended fully into the syringe 102 cutting off the proximal end of the syringe barrel 102-B and proximal end of the plunger 102-P.

Figure 12A:
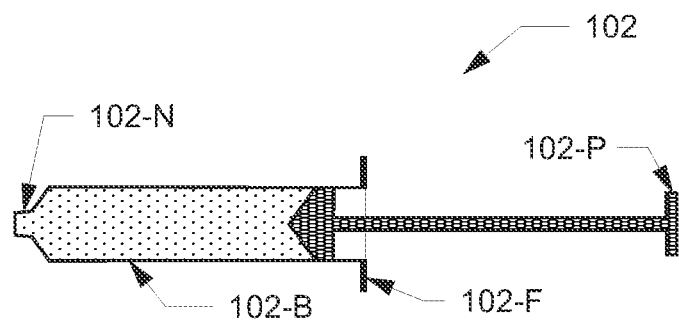
FIGS. 12A-12B show a top view and a side view of a conventional syringe 102.
Figure 12B:
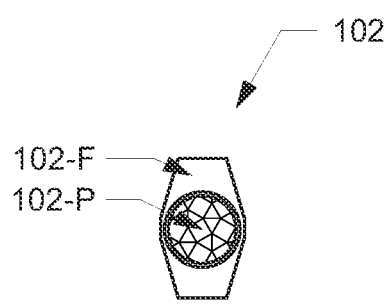

FIGS. 12A-12B show a top view and a side view of a conventional syringe 102.

Figure 13A:
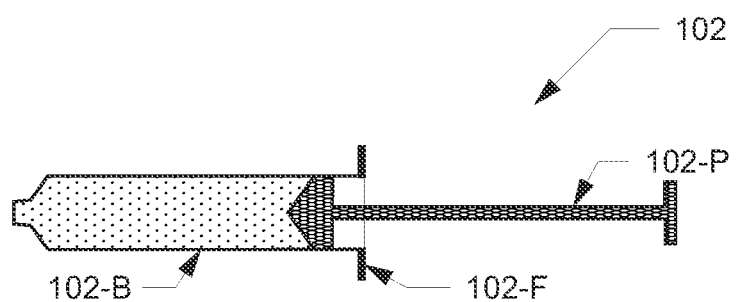
FIGS. 13A-13C show the syringe 102 prior to being cut, just after the syringe is cut, and when the two parts of the syringe 102 which have just been cut have been separated.
Figure 13B:
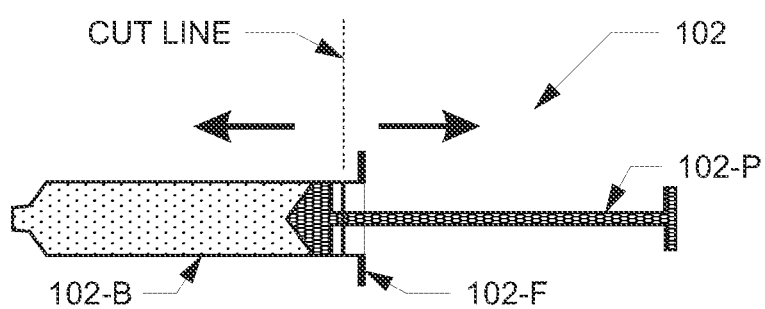
Figure 13C:
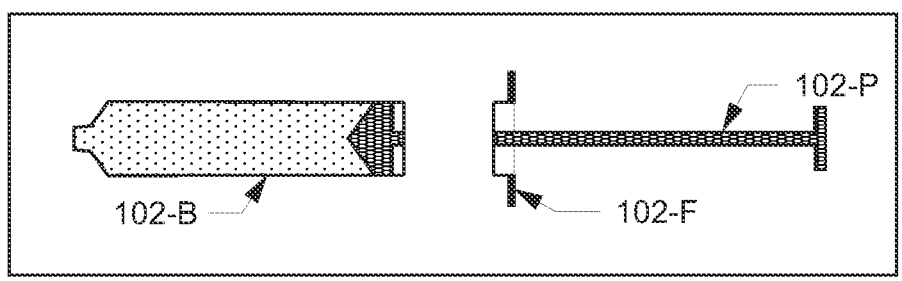

FIGS. 13A-13C show the syringe 102 prior to being cut, just after the syringe is cut, and with the two parts of the syringe 102 are separated. In FIG. 13B the vertical line shows the cut line through the barrel 102-B and plunger 102-P created by blade 116. In FIG. 13C, the left-hand portion shows the syringe 102 containing a specimen and the right-hand portion shows the proximal end of the barrel 102-B and plunger 102-P which have been removed and will be discarded.

While the present disclosure has been described with reference to various embodiments, these embodiments are illustrative, and the scope of the disclosure is not limited to them. Many variations, modifications, additions, and improvements are possible. More generally, embodiments in accordance with the present disclosure have been described in the context of particular embodiments. Functionality may be separated or combined in procedures differently in various embodiments of the disclosure or described with different terminology. These and other variations, modifications, additions, and improvements may fall within the scope of the disclosure as defined in the claims that follow.

The invention claimed is:

1. A cutting device for cutting a syringe, the syringe having a barrel with flanges at a proximal end thereof, the barrel of the syringe containing a liquid specimen, the syringe having a plunger provided in the barrel and sealing the liquid specimen therein, said cutting device comprising:
   a jig for supporting a syringe, the jig including first and second proximal walls and first and second distal walls, the first proximal wall being complimentary shaped to the second proximal wall, the first distal wall being complimentary shaped to the second distal wall;
   a first semi-circular groove defined in the first proximal wall, a second semi-circular groove defined in the second proximal wall, a first semi-circular groove defined in the first distal wall, a second semi-circular groove defined in the second distal wall, the first and second semi-circular grooves in the first and second proximal walls cooperatively define a first through-hole and the first and second semi-circular grooves in the first and second distal walls cooperatively define a second through-hole, the first through-hole have a first diameter and the second through-hole having a second diameter;
   wherein the first and second through-holes are coaxially aligned, the first and second diameters each being configured to receive the barrel of the syringe when the barrel is inserted through the first and second through-holes;
   the first through-hole including a counter bore sized to engage with the barrel flanges when the syringe is fully inserted through the first and second through-holes such that the flanges are supported during the cutting process;
   a third through-hole defined in the first proximal wall, a fourth through-hole defined in the second proximal wall, a fifth through-hole defined in the first distal wall, a sixth through-hole defined in the second distal wall;
   a blade having a planar cutting surface, a seventh through-hole defined through the blade, the planar cutting surface having first and second opposing faces, the blade sandwiched between the proximal and distal walls such that the first face of the planar cutting surface is supported by the distal wall and the second face of the planar cutting surface is supported by the proximal wall, the blade is rotatably mounted between the proximal and distal walls;
   a pin cooperatively received within the third, fourth, fifth, sixth and seventh through holes, said pin defining a pivot point for the blade;
   wherein the blade cuts the proximal end of the syringe with the flanges and a portion of the plunger without contaminating the liquid specimen within the barrel of the syringe.

2. The cutting device of claim 1, further comprising a flange sensor proximal to the counterbore, said flange detector detecting the presence of a flange in the counterbore.

3. A syringe cutting device for cutting a syringe, having a barrel with flanges at a proximal end thereof, the barrel of the syringe containing a liquid specimen, the syringe having a plunger provided in the barrel and sealing the liquid specimen therein, said syringe cutting device comprising:
   a jig for supporting a syringe, the jig including a proximal wall including a first portion and a second portion, a distal wall including a first portion and a second portion, and a blade having a planar cutting surface, the planar cutting surface having first and second opposing faces, the blade sandwiched between the proximal and distal walls such that the first face of the planar cutting surface is supported by the distal wall and the second face of the planar cutting surface is supported by the proximal wall, the blade is rotatably mounted between the proximal and distal walls;
   a first through-hole defined in the first portion of the proximal wall, a second through hole defined in the second portion of the proximal wall, a third through-hole defined in the first portion of the distal wall, and a fourth through-hole defined in the second portion of the distal wall;

a pin inserted into the first, second, third and fourth through-holes thereby allowing the second portion of the proximal wall and the second portion of the distal wall to pivot with respect to the first portion of the proximal wall and the first portion of the distal wall;

the proximal wall having a sixth through-hole, a proximal end of the sixth through-hole including a counterbore, the sixth through-hole cooperatively defined by recess defined in the first portion of the proximal wall and recess in the second portion of the proximal wall when the jig is in a closed position with the first portion of the proximal wall abutting the second portion of the proximal wall, wherein the counterbore has a size and shape configured to receive the flanges of the syringe;

the distal wall having a seventh through-hole, the seventh through-hole cooperatively defined by semicircular recess defined in the first portion of the distal wall and semicircular recess in the second portion of the distal wall when the jig is in a closed position with the first portion of the distal wall abutting the second portion of the distal wall, wherein a diameter of the seventh through-hole is configured to approximate a diameter of the barrel of the syringe;

wherein the counterbore is configured to engage and support the syringe flanges when the syringe is fully inserted into the sixth and seventh through-holes;

wherein the blade cuts the proximal end of the syringe barrel with the flanges and syringe plunger without contaminating the liquid specimen within the barrel.

4. The cutting device of claim 3, further comprising a fifth through-hole defined in the blade, the pin extending through the fifth through-hole.

5. The cutting device of claim 3, further comprising a flange sensor proximal to the counterbore, said flange detector detecting the presence of the flange in the counterbore.

* * * * *